(12) United States Patent
Cinbis et al.

(10) Patent No.: US 8,548,543 B2
(45) Date of Patent: Oct. 1, 2013

(54) SYMMETRICALLY PACKAGED OPTICAL SENSORS FOR IMPLANTABLE MEDICAL DEVICES

(75) Inventors: Can Cinbis, Shoreview, MN (US); Jonathan L. Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 414 days.

(21) Appl. No.: 12/915,984

(22) Filed: Oct. 29, 2010

(65) Prior Publication Data
US 2012/0108923 A1 May 3, 2012

(51) Int. Cl.
*A61B 5/1455* (2006.01)

(52) U.S. Cl.
USPC .......................................... 600/310; 600/322

(58) Field of Classification Search
USPC ................................................ 600/310–344
See application file for complete search history.

(56) References Cited

U.S. PATENT DOCUMENTS

| 4,202,339 | A  | 5/1980  | Wirtzfeld et al. |
| 4,281,645 | A  | 8/1981  | Jöbsis |
| 4,467,807 | A  | 8/1984  | Bornzin |
| 4,730,389 | A  | 3/1988  | Baudino et al. |
| 4,880,304 | A  | 11/1989 | Jaeb et al. |
| 5,329,922 | A  | 7/1994  | Atlee, III |
| 5,556,421 | A  | 9/1996  | Prutchi et al. |
| 5,902,326 | A  | 5/1999  | Lessar et al. |
| 6,144,866 | A  | 11/2000 | Miesel et al. |
| 6,198,952 | B1 | 3/2001  | Miesel |
| 2009/0156912 | A1 | 6/2009 | Kuhn et al. |
| 2009/0156918 | A1 | 6/2009 | Davis et al. |
| 2010/0185262 | A1 | 7/2010 | Kuhn et al. |

OTHER PUBLICATIONS

International Search Report for PCT Patent Application No. PCT/US2011/034538, Jul. 27, 2011; 5 pgs.

*Primary Examiner* — Eric Winakur
*Assistant Examiner* — Marjan Fardanesh
(74) *Attorney, Agent, or Firm* — Evans M. Mburu

(57) ABSTRACT

Implantable medical devices and methods include an optical sensor that includes at least two optical sensor portions. The light emitting devices of the optical sensor are distributed among the at least two optical sensor portions.

20 Claims, 6 Drawing Sheets

ND DEVICES

The disclosure herein relates to optical sensors, such as those used in an implantable medical device to sense physiological conditions.

Implantable medical devices (IMDs) for monitoring a physiological condition and/or delivering a therapy include one or more physiological sensors. Physiological sensors used in conjunction with an IMD provide one or more signals related to one or more physiological conditions from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors may be employed in IMDs as physiological sensors configured to detect changes in light modulation by, for example, a body fluid or tissue measurement volume due to a change in a physiological condition in the body fluid or tissue. Such optical sensors can be used, for example, to detect changes in metabolite levels in the blood, such as oxygen saturation levels or glucose level, or changes in tissue perfusion.

Monitoring such physiological conditions provides useful diagnostic measures and may be used in managing therapies for treating a medical condition. For example, a decrease in blood oxygen saturation or in tissue perfusion may be associated with insufficient cardiac output or respiratory function. Thus, monitoring such conditions may allow an implantable medical device to respond to a decrease in oxygen saturation or tissue perfusion, for example, by delivering electrical stimulation therapies to the heart to restore a normal hemodynamic function.

Examples of implantable optical sensors are generally disclosed in commonly assigned U.S. Pat. No. 6,198,952 issued on 6 Mar. 2001 to Miesel entitled "Multiple Lens Oxygen Sensor for Medical Electrical Lead;" U.S. Pat. Pub. No. 2010/0185262 published 22 Jul. 2010 to Kuhn et al. entitled "Co-Location of Emitters and Detectors and Method of Operation;" U.S. Pat. No. 6,144,866 issued on 7 Nov. 2000 to Miesel et al. entitled "Multiple Sensor Assembly for Medical Electrical Lead;" and U.S. Pat. Pub. No. 2009/0156912 published 18 Jun. 2009 to Kuhn et al. entitled "Implantable Optical Sensor and Method for Manufacture," all hereby incorporated herein by reference in their entirety. Further, for example, cardiac pacemakers that respond to changes in blood oxygen saturation as measured by an optical sensor are generally disclosed in U.S. Pat. No. 4,202,339 issued on 13 May 1980 to Wirtzfeld entitled "Cardiac Pacemaker" and in U.S. Pat. No. 4,467,807 issued on 28 Aug. 1984 to Bornzin entitled "Rate Adaptive Demand Pacemaker," both of which are incorporated herein by reference in their entirety.

It is desirable to provide implementation of implantable optical sensors in a manner that promotes effective sensing capabilities while also providing such optical sensors in a small package size. Typical light sources, such as light emitting diodes (LEDs) and vertical-cavity surface-emitting lasers (VCSELs) rely on semiconductor materials that have very high optical absorption coefficients (e.g., III-V semiconductors). When implementing optical sensors that rely on multiple optical emitters and multiple windows, placement of multiple dies next to each other (e.g., tightly packing such dies) decreases optical efficiency due to the high absorption coefficients. Further, spatially separating them to achieve higher optical efficiency results in a larger undesirable package.

SUMMARY

The disclosure herein relates generally to optical sensors, devices, systems, and methods for sensing physiological conditions, e.g., as part of an implantable medical device. For example, such optical sensors may sense one or more physiological conditions (e.g., a decrease in blood oxygen saturation), and further, for example, therapy may be initiated or adjusted based on such sensing.

An exemplary implantable medical device described herein may include a hermetically sealed housing (e.g., a hermetically sealed housing including one or more sensor openings defined therethrough) and an optical sensor configured to generate a signal representative of a physiological condition. The optical sensor may include first and second optical sensor portions. For example, the first optical sensor portion may include at least one light emitting device and at least one light detecting device (e.g., the at least one light emitting device and the at least one light detecting device being configured to emit light through a first optical window located within the one or more sensor openings and to detect light through the first optical window, respectively). The second optical sensor portion, for example, may include at least one light emitting device and at least one light detecting device (e.g., the at least one light emitting device and the at least one light detecting device being configured to emit light through a second optical window located within the one or more sensor openings and to detect light through the second optical window, respectively). The at least one light emitting device of the first optical sensor portion is configured to emit light at a first wavelength and the at least one light detecting device of the second optical sensor portion is configured to detect light of the first wavelength. Further, the at least one light emitting device of the second optical sensor is configured to emit light of a second wavelength and the at least one light detecting device of the first optical sensor is configured to detect light of the second wavelength. The device further may include a control module coupled to the first and second optical sensor portions to control the emission and detection of light through the first and second optical windows.

In another exemplary embodiment of an implantable medical device, the device may include a hermetically sealed housing (e.g., a hermetically sealed housing including one or more sensor openings defined therethrough) and an optical sensor configured to generate a signal representative of a physiological condition. The optical sensor may include at least two optical sensor portions (e.g., each of the at least two optical sensor portions for emitting and detecting light through a corresponding optical window located within the one or more sensor openings). Further, each of the at least two optical sensor portions includes at least one light emitting device (e.g., one, two or more, etc.) to emit light through the corresponding window and at least one light detecting device to detect light through the corresponding window (e.g., the number of light emitting devices in each optical sensor portion may be equal, or one optical sensor portion may have one more light emitting device than the other optical sensor portions). Still further, the at least one light emitting device of each optical sensor portion emits light at a wavelength that is different than the at least one light emitting device of the other optical sensor portions and the at least one light detecting device of each optical sensor portion detects light at a wavelength emitted by at least one light emitting device of the other optical sensor portions. The device may further include a control module coupled to the optical sensor to control the emission and detection of light.

In one embodiment of the device, the at least one light detecting device of each optical sensor portion may include a wideband light detector configured to detect light at a wavelength emitted by at least one light emitting device of the other optical sensor portions and to detect light emitted by the at least one light emitting device of the optical sensor portion with which it is co-located. Further, such an embodiment may include a control module configured to monitor light output level of the at least one light emitting device of the optical sensor with which it is co-located and control variation of light output levels based on the monitored light output level.

One exemplary method for use in an implantable medical device having an optical sensor may include enabling emission of light at a first wavelength by the at least one light emitting device of a first optical sensor portion for detection by at least one light detecting device of a different optical sensor portion and enabling emission of light at a second wavelength by the at least one light emitting device of a second optical sensor portion for detection by at least one light detecting device of a different optical sensor portion. Further, for example, in one embodiment, the method may include providing a therapy to a patient based at least in part on light detected by the at least one light detecting device.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
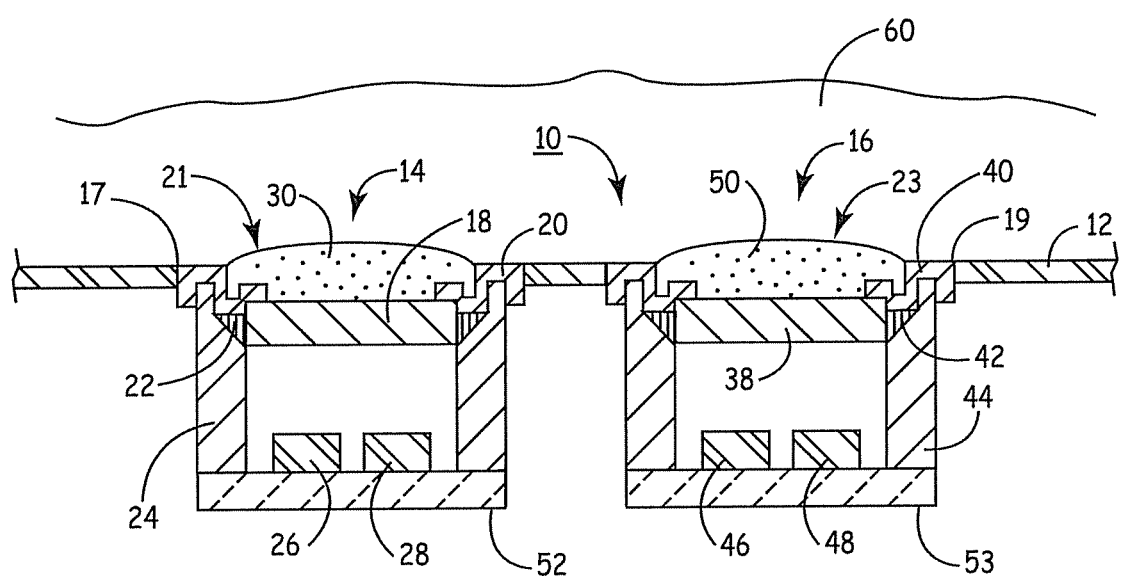
FIG. 1 is a side sectional view of one exemplary embodiment of an optical sensor for use in a medical device, e.g., an implantable medical device.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Figure 3:
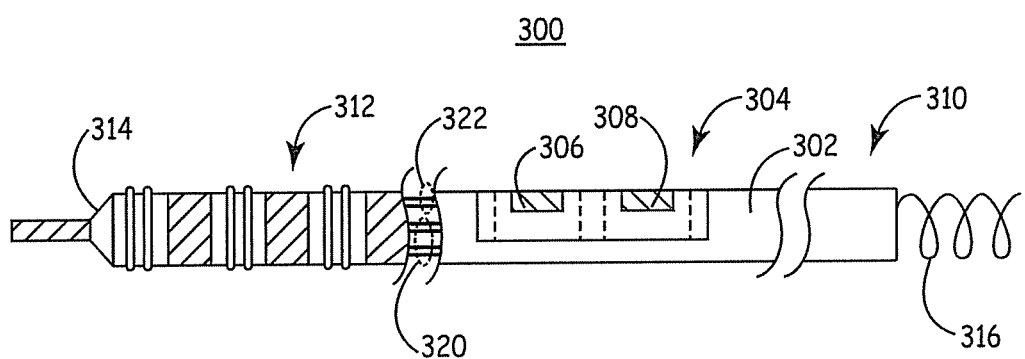
FIG. 3 is a plan view of one exemplary embodiment of a medical lead including an optical sensor, such as that shown in FIGS. 1 and 2.
Figure 4:
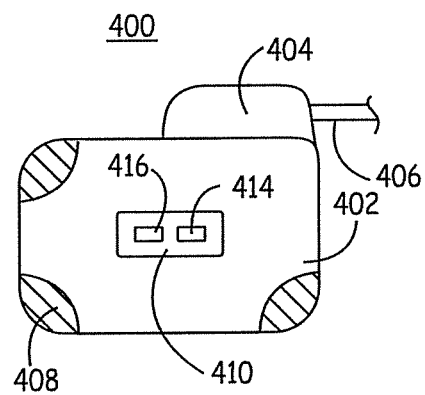
FIG. 4 is a plan view of one exemplary embodiment of an IMD including an optical sensor, such as that shown in FIGS. 1 and 2.

FIG. 1 is side sectional view of an exemplary embodiment of an optical sensor 10. Optical sensor 10 may be incorporated in a housing of an implantable medical device (e.g., the case of an implantable medical device as shown in FIG. 4), such as in a subcutaneously implanted pacemaker or ICD housing, may be carried by a housing of medical electrical lead (e.g., the lead body connected to an implantable medical device as shown in FIG. 3), or may be part of it's own autonomous module independent of a therapy, or combined with other sensors.

Sensor 10 includes a first optical sensor portion 14 including at least one light emitting device 26 and at least one light detecting device 28 and a second optical sensor portion 16 including at least one light emitting device 48 and at least one light detecting device 46. As shown more specifically in FIG. 1, each of the optical sensor portions 14, 16 include a single light emitting device and a single light detecting device. For example, each of the optical sensor portions 14, 16 are substantially symmetric with respect to the number of light emitting devices in each of the optical sensor portions 14, 16. The light emitting devices of optical sensor 10 are equally distributed between the optical sensor portions 14, 16 of the optical sensor 10.

The optical sensor portions 14, 16 are incorporated into a hermetically sealed capsule or housing 12 for enclosing the optical sensor components. Each optical sensor portion 14 and 16 includes a lens 18 and 38, respectively, for passing emitted light from the light emitting devices 26, 48 and passing scattered light to the light detecting devices 28, 46. Lens 18 and lens 38 are commonly formed, for example, from sapphire and are hermetically sealed within sensor openings 17 and 19 of housing 12 using ferrules 20 and 40, respectively, bonded to lenses 18 and 38 at joints 22 and 42. Joints 22 and 42 may be gold braze joints or foamed using a polymer adhesive depending on the ferrule material and other manufacturing processes used in fabricating sensor 10. In other words, a first optical window 21 of optical sensor portion 14 is provided within sensor opening 17 and a second optical window 23 is provided within sensor opening 19.

Housing 12 (e.g., a case of an IMD) may be formed, for example, from titanium, stainless steel, ceramic, glass, or a rigid polymer. In one embodiment, housing 12 and ferrules 20 and 40 are each formed from titanium. Ferrules 20 and 40 are then welded within openings formed in housing 12 to maintain hermeticity of sensor 10. The optical window assembly generally disclosed in U.S. Pat. No. 5,902,326 (Lessar, et al.), hereby incorporated herein by reference in its entirety, may be implemented to provide optical windows. Transparent polymeric seals 30 and 50 may be formed over lenses 18 and 38 and ferrules 20 and 40, respectively. Seals 30 and 50 may be formed for example, from silicone rubber. Seals 30 and 50 protect gold braze joints 22 and 42 from the corrosive effects of bodily fluids and may provide a smooth, convex surface thereover.

Light emitting devices herein (also sometimes referred to as opto-electronic devices, opto-electronic components, light sources, or light emitting elements) may include any electrical circuit component(s) capable of emitting light in response to an applied voltage or current, including, for example, light emitting diodes (LEDs), vertical cavity surface emitting lasers (VCSELs), photoresistors or light dependent resistors, photodiodes, phototransistors, photovoltaic cells, or charge-coupled devices, etc. Light detecting devices herein (also sometimes referred to as opto-electronic devices, opto-electronic components, detectors, or light detecting elements) may include any electrical circuit component(s) capable of generating current or voltage in response to exposure to light, including, for example, LEDs, VCSELs, photoresistors or light dependent resistors, photodiodes, phototransistors, photovoltaic cells, charge-coupled devices, avalanche detectors, etc.

For example, the first optical sensor portion 14 may include a light emitting device 26 (e.g., a light source embodied as an LED) and a light detecting element 28 (e.g., a light detector embodied as an silicon photodiode) co-located with the light emitting device 26 (e.g., co-located to operate with respect to the same window, or in other words, emit light and detect light through the same window as part of the same window package). Devices 26 and 28 may be mounted on a printed circuit board 52 to enable the necessary connections for applying a voltage to light emitting device 26 to cause light emission and allowing one or more signals to be carried from light detecting device 28 representative of detected light. A wall 24 may surround the devices 26 and 28 to prevent absorption of light and promote transmission of light through lens 18 toward adjacent body fluid or tissue volume 60 and to promote light traveling through lens 18 to fall on light detecting device 28. Body fluid or tissue volume 60 may correspond to any bodily fluid, such as blood, or body tissue, such as skeletal muscle, neural tissue, myocardium, etc. Wall 24 may be formed from a rigid, non-transparent material, such as a liquid crystal polymer. Alternatively, wall 24 may be formed from other non-transparent materials, for example a polymer material formed as a molded component. Wall 24 may be coupled to circuit board 52. For example, wall 24 may be coupled to printed circuit board 52 using a hard die coat dam holding wall 24 to the board 52.

Likewise, for example, the second optical sensor portion 16 may include a light emitting device 48 (e.g., a light source embodied as an LED) and a light detecting device 46 (e.g., a light detector embodied as a silicon photodiode) co-located with the light emitting device 48 (e.g., co-located to operate with respect to the same window, or in other words, emit light and detect light through the same window as part of the same window package). Devices 46 and 48 may be mounted on a printed circuit board 53 to enable the necessary connections for applying a voltage to light emitting device 48 to cause light emission and allowing one or more signals to be carried from light detecting device 46 representative of detected light. A wall 44 may surround the devices 46 and 48 to prevent absorption of light and promote transmission of light through lens 38 toward adjacent body fluid or tissue volume 60 and to promote light traveling through lens 38 to fall on light detecting device 46. Wall 44 may be formed like that of wall 24 and may be coupled to circuit board 53 in a manner like that of wall 24 to circuit board 52. In one embodiment, wall 44 may share a common side with wall 24, or alternatively, be separated therefrom by a particular distance.

It will be recognized that various structures may be used to construct the optical sensors described herein. The disclosure herein is not limited to the particular structural elements described for forming the optical sensors. For example, various processes and structures may be used to provide for hermetically sealed windows within housings described herein, various layouts of light emitting and detecting devices may be used, the sensor portions may be positioned at various locations of a housing (e.g., side by side, facing one another, etc.), various spacing between windows may be used, various types of emitting and detecting devices may be used, etc.

In one or more embodiments, for example, light emitting devices 26, 48 may be formed from a direct band-gap semiconductor that emits narrow spectrum light when electrically biased in the forward direction of the p-n junction. On the other hand, light detecting devices 28 and 46 are biased to generate current or voltage upon exposure to light, allowing devices 28 and 46 to function as light detectors.

The two light emitting devices 26 and 48 emit light corresponding to two different wavelengths. For example, in one embodiment, in which optical sensor 10 is used for sensing blood oxygen saturation, one of light emitting devices 26 and 48 may emit red light and the other emit infrared light. Further, for example, in another embodiment, in which optical sensor 10 is used for sensing tissue perfusion, an additional third light emitting device may be included (see other further multiple light emitting device embodiments described herein). Emitted light passes through the corresponding optical window 21, 23 (e.g., including lens 18, 38), respectively, and enters body fluid or tissue volume 60.

It is recognized that one or more light emitting devices may be included in each of the optical sensor portions 14, 16. The number of light emitting devices and corresponding emission wavelengths will be selected according to the requirements of a particular application and will depend on the physiological condition being monitored. In at least one embodiment, such light emitting devices (e.g., light sources) are equally distributed among the available optical sensor portions of the optical sensor 10. However, in other embodiments, one optical sensor portion may have one more light emitting device than other optical sensor portions. For example, the optical sensor may include five wavelengths (e.g., the fourth and fifth wavelength being for a second derivative, an oxygen index or any other algorithm). In such a case, one optical sensor portion may include three light emitting devices and the other optical sensor portion may include the other two light emitting devices.

Light detecting device 28 may be selected to be sensitive to the wavelength of light emitted by at least the light emitting device 48, and may also be sensitive to the light emitted by the light emitting element 26 co-located therewith (or any other wavelength of interest). Light detecting device 46 may be selected to be sensitive to the wavelength of light emitted by at least the light emitting device 26, and may also be sensitive to the light emitted by the light emitting element 48 co-located therewith (or any other wavelength of interest). For example, in at least one embodiment, each of the optical sensor portions may include at least one light detecting device that is sensitive to the light emitted by light sources of other optical sensor portions as well as the light emitted by the light emitting elements co-located therewith in the same optical sensor portion (e.g., to track light output levels).

As shown in FIG. 1, a symmetrical light path arrangement exists such that the light path length between light emitting device 26 of the first optical sensor portion 14 and the light detecting device 46 of the second optical sensor portion 16 and the light path length between light emitting device 48 of the second optical sensor portion 16 and the light detecting device 28 of the first optical sensor portion 14 are substantially symmetrical (e.g., light path lengths are about equal). In at least one specific embodiment, for example, the light detecting devices 28 and 46 may be silicon photodiodes, used with a time multiplexed sampling process including light detection corresponding to a light emitting device off state (e.g., an off state for an emitting LED) for one or more of the light emitting devices to measure ambient light. Such an ambient light measurement may, for example, be subsequently subtracted from other light measurements for one or more wavelengths to correct for the existence of any ambient light.

In another embodiment, the light detecting device 46 of the second sensor portion 16 is sensitive to the same wavelength of light emitted by LED 26 of the first sensor portion 14 and the other light detecting device 28 of first sensor portion 14 is sensitive to the same wavelength emitted by light emitting device 48 of the second sensor portion 16. For example, in one embodiment, in which optical sensor 10 is used for sensing blood oxygen saturation as described above, light detecting device 46 is sensitive to red light emitted by light emitting device 26 and the other of light detecting device 28 is sensitive to infrared light emitted by light emitting device 48. Further, for example, in another embodiment, in which sensor assembly 10 is used for sensing tissue perfusion, additional LEDs may be included. In addition, in at least one embodiment, each of the optical sensor portions include at least one light detecting device that is sensitive to the light emitted by light sources of other optical sensor portions but not sensitive to light emitted by light sources within the same optical sensor portion. For example, in such a manner, with use of an LED as a detector, the detector itself may provide the filtering to reduce influence of ambient light.

Conventionally, multiple light emitting dies (e.g., light sources) were placed next to each other in a single window and one or more light detecting dies were located in a separate receiving window. Placement of such light emitting dies next to each other in the same window decreases the optical efficiency of such devices and may necessitate larger packages to accommodate the components. By distributing the light sources (e.g., emitting light at different wavelengths) among two or more windows (e.g., equally or with one window including one more light source than the other(s)) with one or more light receiving detectors located in each of such windows (e.g., detectors sensitive to wavelengths of light sources emitting through other windows), light absorption effect due to crowding can be reduced and smaller package size may be feasible. For example, to implement a two source/one detector optical sensor design, one of the sources with a detector can be placed in one window package and the other source can be placed with another detector in another window package making the window geometry substantially identical and smaller. Such a two source embodiment is shown in FIG. 1. Likewise, for example, to implement a four source/one detector optical sensor design, two of the sources with a detector can be placed in one window package and the other two sources can be placed with another detector in another window package making the window geometry substantially identical and smaller. Such a four source embodiment shall be described with reference to FIG. 2A.

Such configurations yield light detectors co-located with light emitters to allow for a reference measurement. Further, smaller windows with fewer components tend to be overall more optically efficient, simply because the light is concentrated into a smaller area.

Still further, another advantage of such distributed light sources is to provide about the same optical path length for each light emitting device/light detecting device combination. For example, conventionally, when four LEDs were provided in one package in a square pattern (e.g., in a first window) and a detector was provided in another package (e.g., a second window), two of the LEDs were closer to the detector than the other two LEDs, resulting in different optical sensor probe volumes (e.g., due to different optical path lengths). When the light emitting devices are placed geometrically symmetrical such that all four LED/detector path lengths are about the same, then the optical sensor probe volumes for LED/detector combinations are not different. For example, as shown in the four light emitting device embodiment of FIG. 2A, if the light emitting devices and light detecting devices are rearranged as shown in FIG. 2B, then each light emitting device/light detecting device combination (e.g., 26/46, 27/46, 47/28, and 48/28) has about the same optical path length and window package size is minimized.

Alternatively, although package size may not be minimized, all four light emitting devices (e.g., two or more light emitting devices) could be provided in one window package in a configuration that would create optical paths between each of such light emitting devices and a detecting device provided in another window package that are about equal. For example, the light emitting devices could be placed in a line, or even an arc centered on the light detecting device as shown in FIG. 2C (e.g., light emitting devices 26-27 and 47-48 being in an arc with respect to light detecting device 46).

Light emitted from optical sensor portion 14 is scattered and absorbed by the body fluid or tissue volume 60. Scattered light travels through lens 38 to light detecting device 46. Scattered light that corresponds to wavelengths to which light-detecting device 46 is responsive will cause the light detecting device 46 to generate current or voltage corresponding to the intensity of the received light. Light modulation due to a physiological change may result in a signal generated by the light detecting device 46 that may be correlated to a changing physiological condition. Likewise, light emitted from optical sensor portion 16 is scattered and absorbed by the body fluid or tissue volume 60. Scattered light travels through lens 18 to light detecting device 28. Scattered light that corresponds to wavelengths to which light detecting device 28 is responsive will cause the light detecting device 28 to generate current or voltage corresponding to the intensity of the received light. Light modulation due to a physiological change may result in a signal generated by the light detecting device 28 that may be correlated to a changing physiological condition.

As such, light wavelengths scattered by body fluid or tissue volume 60 will cause a light detecting device responsive to selected light wavelengths to emit a signal useful in measurement of one or more physiological conditions (or changes in such physiological conditions) in the body fluid or tissue volume 60. For example, in an optical sensor for estimating oxygen saturation in blood, the intensity of red light scattered by the body fluid or tissue and detected is dependent on the concentration of oxygenated hemoglobin in the blood. The intensity of infrared light scattered by the body fluid or tissue can be made independent of the concentration of oxygenated hemoglobin by proper choice of wavelength (e.g., 800 nm). The scattered red light detected may be normalized by the infrared light detected to correct for variables such as total hemoglobin, tissue overgrowth and blood flow velocity or other artifacts.

Circuit boards 52, 53 are shown upon which optical sensor portions 14, 16 are assembled, respectively. Although not shown in FIG. 1, it will be understood by one having skill in the art that the circuit boards 52, 53 may include integrated circuitry electrically coupled to the light emitting devices to deliver driver signals applied to light emitting devices and to activate light emitting devices. Likewise, integrated circuitry included on circuit boards 52, 53 may be coupled to light detecting devices to receive the current or voltage generated by light detecting devices in response to scattered light incident thereon and providing the signal to processing circuitry configured to perform one or more algorithms with respect thereto (e.g., to detect a change in a physiological condition using the signal, provide a condition measurement, for use in controlling therapy based thereon, etc.). Integrated circuitry may, for example, include amplification, analog-to-digital converters, flash memory for digitizing the analog signal and providing the digitized signal to processing circuitry, etc.

It will be recognized that the optical sensor configured to generate a signal representative of a physiological condition may comprise two, or more than two, optical sensor portions with each of the optical sensor portions being configured for emitting and detecting light through a corresponding optical window located within a sensor opening of the housing. Generally, at least in one embodiment, each of the optical sensor portions include at least one light emitting device to emit light through the corresponding window and at least one light detecting device to detect light through the corresponding window. Further, the light emitting devices of the optical sensor are distributed among each optical sensor portion (e.g., if four light sources, then two light sources are provided in each optical sensor portion, or, in other words, equally within each window package; if five light sources, then two light sources may be provided in a first optical sensor portion and three light sources may be provided in another optical sensor portion; etc.). At least in one embodiment, the one or more light emitting devices of each optical sensor portion emit light at a wavelength that is different than the one or more light emitting devices of the other optical sensor portions and the one or more light detecting devices of each optical sensor portion detect light being emitted from another optical sensor portion. In other words, the one or more one light detecting devices of each optical sensor portion may detect light at a wavelength corresponding to a wavelength of at least one light emitting device of the other optical sensor portions. Further, each of the optical sensor portions may include at least one light detecting device that is sensitive to the light emitted by light sources of other optical sensor portions as well as the light emitted by the light emitting elements co-located therewith in the same optical sensor portion (e.g., a wideband light detector to track light output levels of co-located light sources, as well as detect light emitted by other optical sensor portions).

Figure 2A:
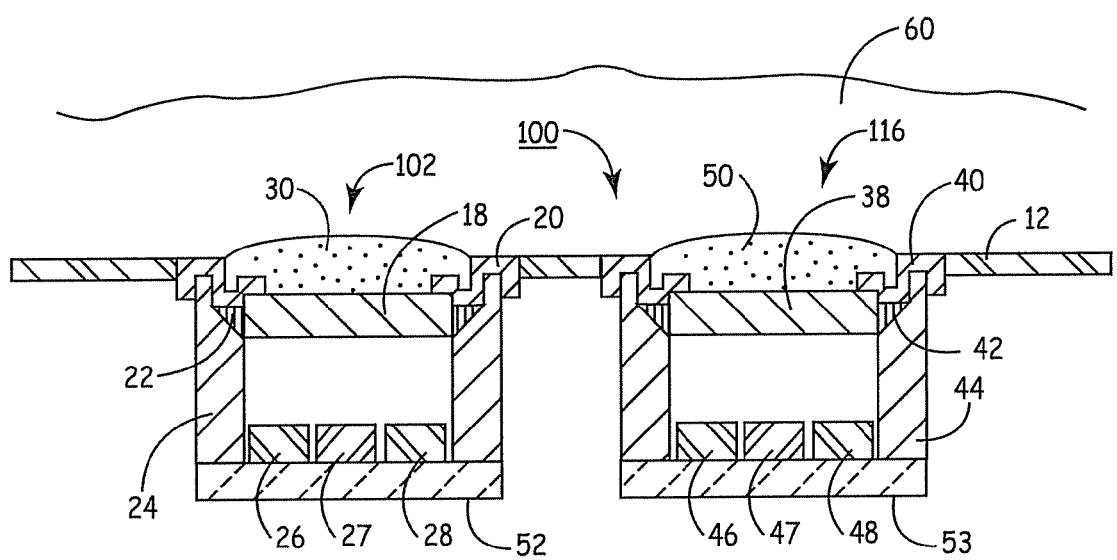
FIG. 2A is a side sectional view of another exemplary embodiment of an optical sensor for use in a medical device, e.g., an implantable medical device.
Figure 2B:
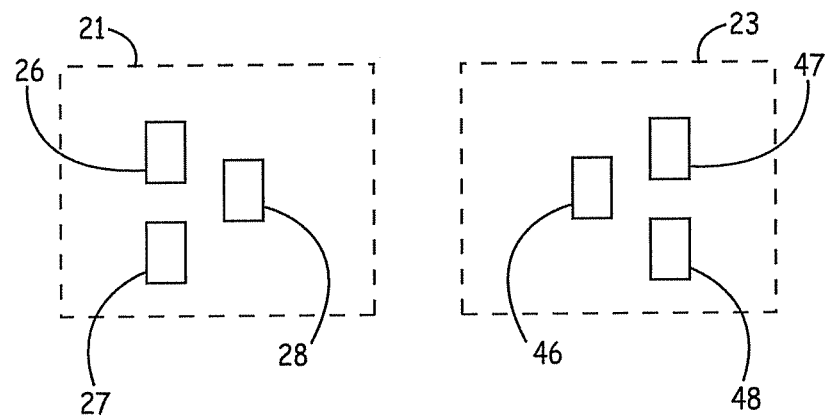
FIGS. 2B-2C are top views of optical sensor layouts.
Figure 2C:
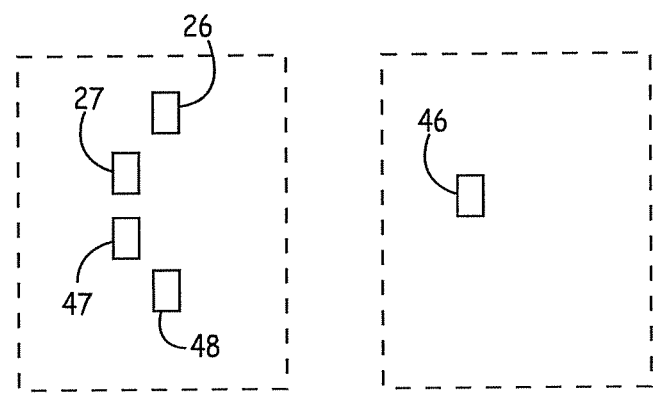

For example, an optical sensor 100 shown in FIG. 2A includes first and second optical sensor portions 102, 116 which are substantially similar to the optical sensor portions 14, 16 shown in FIG. 1, except that such sensor portions 102, 116 include an additional light emitting device 27 in the first optical sensor portion 102 and an additional light emitting device 47 in the second optical sensor portion 116. As such, a four light source embodiment is shown.

It will be recognized that more than four light sources may be distributed between the two optical sensor portions, or may be distributed between the two optical sensor portions and one or more additional optical sensor portions emitting light through and detecting light through corresponding windows. In at least one or more embodiments, each of the at least two optical sensor portions are substantially of identical geometry. Being substantially identical in geometry refers to the geometries of the window packages being structurally similar with similar overall device layout (e.g., equal numbers of light emitting and light detecting devices being located in about the same positions) but not necessarily the same in function (e.g., such light emitting and light detecting devices being operable for emitting and detecting light of different wavelengths). In the case of an even number of light emitting elements, substantially identical in geometry refers to the geometries being structurally the same with the device layout also being the same (e.g. equal numbers of light emitting and light detecting devices being located in about the same positions). However, in the case of an odd number of light emitting elements, substantially identical in geometry refers to the geometries being structurally similar with one of the optical sensor portions having one more additional light emitting element than the other(s) and with the device layout also being similar except for the additional light emitting element in one of the optical sensor portions (e.g., two of the light emitting elements in one optical sensor portion being located in about the same position as three light emitting elements in another optical sensor portion).

As shown in FIG. 2, each of the two light emitting devices 26, 27 of the optical sensor portion 102 are configured to emit light at different wavelengths (e.g., device 26 may emit light at a wavelength of a set of wavelengths and the device 27 may emit light at a wavelength of the set of wavelengths that is different than the device 26 of the optical sensor portion 102). Likewise, each of the two light emitting devices 47, 48 of the optical sensor portion 116 are configured to emit light at different wavelengths (e.g., device 48 may emit light at a wavelength of a set of wavelengths and the device 47 may emit light at a wavelength of the set of wavelengths that is different than the device 48 of the optical sensor portion 116). Further, the wavelengths of light emitted by the first optical sensor portion 102 may be different than the wavelengths of optical light emitted by the second optical sensor portion 116 (e.g., the first set of wavelengths may be different than the second set of wavelengths).

Still further, as shown in FIG. 2, light emitted from optical sensor portion 102 is scattered and absorbed by the body fluid or tissue volume 60. Scattered light travels through lens 38 to light detecting device 46, e.g., a photodiode. Scattered light that corresponds to wavelengths to which light detecting device 46 is responsive will cause the light detecting device 46 to generate current or voltage corresponding to the intensity of the received light.

Figure 5:
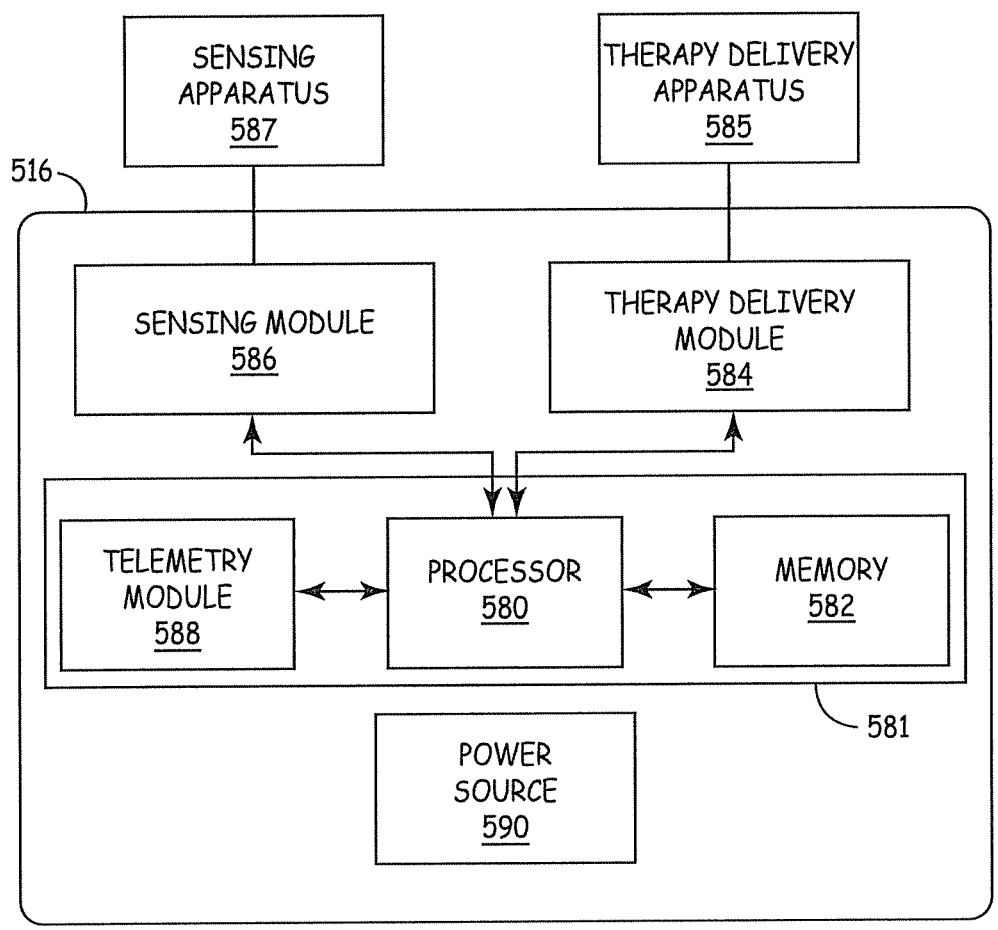
FIG. 5 is a functional block diagram of an exemplary IMD (e.g., such as that shown in FIG. 4) including sensing apparatus, such as an optical sensor as shown in FIGS. 1-4.

For example, light detecting device 46 may be configured to be sensitive to either or both of the wavelengths emitted by light emitting devices 26, 27, as well as light emitting devices 47, 48. In other words, light detecting device 46 may be configured as a wideband light detector. For example, the wide band light detector may be used to detect light from any one or more of the light emitting devices (e.g., light sources) with such detected light being used for one or more various purposes (e.g., including sensing of one or more physiological parameters, tracking light output, or detecting ambient light for signal correction purposes). For example, the one or more light emitting devices may be time-multiplexed (e.g., under control of a control module, such as shown in FIG. 5) to prevent interference during detection by the wideband detector of one or more particular wavelengths to be detected.

Still further, the light detecting device 46 used in sensor portion 116 may be multiple light detector components tuned to wavelengths emitted by different optical sensor portions (and, at least in one embodiment, also to the wavelengths emitted by co-located light sources). For example, if the detector components are each tuned to a particular wavelength, one can activate all the light sources at once and detect them at once enabling simultaneous measurements. For example, this may be beneficial in situations where the physiologic variable being measured is changing fast. Further, it may also be advantageous in reducing sensitivity to ambient light.

Light modulation may result in a signal generated by the light detecting device 46 that, for example, may be correlated to a physiological parameter or a changing physiological condition. Such correlation may be useful in providing therapy to a patient.

Likewise, light emitted from optical sensor portion 116 is scattered and absorbed by the body fluid or tissue volume 60. Scattered light travels through lens 18 to light detecting device 28. Scattered light that corresponds to wavelengths of which light-detecting device 28 is responsive will cause the device 28 to generate current or voltage corresponding to the intensity of the received light. For example, the light detecting device 28 of optical sensor portion 116 may be a light detecting device such as a wideband light detector as described herein, or may be multiple detecting components tuned to particular wavelengths as described herein (e.g., with respect to light detecting device 46). Light modulation may result in a signal generated by the light detecting device 28 that, for example, may be correlated to physiological parameter or a changing physiological condition.

At least in one embodiment, since a light detecting device is co-located with one or more light emitting devices (e.g., co-located to operate with respect to the same window, or in other words, emit light and detect light through the same window of a window package), it is possible to track light output from one or more of the co-located light emitting devices. In other words, for example, with respect to FIG. 1, light detecting device 28 of optical sensor portion 14 may include a wideband light detector configured to detect light at a wavelength emitted by light emitting device 48 of the other optical sensor portion 16 and to detect light emitted by the light emitting device 26 co-located with the light detecting device 28 in optical sensor portion 14. As such, for example, a control module (e.g., control module 581) may be configured to monitor light output level of the light emitting device 26 of the optical sensor portion 14 with which it is co-located and control variation of light output levels based on the monitored light output level. Any light detecting devices described herein may be configured in such a manner.

FIG. 3 is a plan view of a medical lead including an optical sensor 304, such as, for example, that shown in FIGS. 1 and 2. Lead 300 includes an elongated body 302 extending between a proximal end 312 and a distal end 310. The optical sensor 304 may be positioned along lead body 302, typically near distal end 310. The optical sensor 304 includes at least two windows 306 and 308 through which light is emitted and through which scattered light travels to be detected. Windows 306 and 308 may correspond, for example, to the windows 21, 23 as shown in FIG. 1.

The lead body 304 may carry, for example, separately insulated conductor pairs 322 and 320 between a proximal connector assembly 314 and sensor 304. Conductor pair 322 may be provided for carrying drive signals from proximal connector assembly 314 to light emitting sources (e.g., LEDs or other light sources). Conductor pair 320 may be provided for carrying current generated by light detecting devices (e.g., photodiodes detecting light) to proximal connector assembly 314. Connector assembly 314 may be coupled to an implantable medical device to thereby couple the optical sensor 304 to associated sensor driver/signal processing circuitry (not shown in FIG. 3) included in, for example, a medical device (e.g., an implantable medical device).

The lead 300 is shown having a distal fixation member 316 for anchoring the position of distal end 310 at a targeted implant location. In some embodiments, fixation member 316 may serve as an electrode and be coupled to an insulated conductor extending to proximal connector assembly 314. In various embodiments, lead 300 may include other sensors and/or electrodes. As such, it is recognized that the particular configurations of lead body 302, conductors carried by the lead body and the proximal connector assembly 314 will depend on the particular configuration of electrodes and sensors carried by lead 300.

FIG. 4 is a plan view of an IMD 400 in which an optical sensor 410 may be incorporated in the housing 402 (e.g., case) of device 400. IMD 400 includes hermetically sealed housing 402, a connector block 404, and may include an electrode array 408 or other physiological sensors incorporated in housing 402. The optical sensor 410 is hermetically sealed within one or more sensor openings in IMD housing 402 such that windows 414 and 416 associated with light emitting and light detecting portions of sensor 410 are exposed to adjacent tissue or body fluid when the IMD 400 is implanted in a subcutaneous, submuscular, transvenous, intracardiac or other internal body location. Electrical connections (not shown) between sensor 410 and IMD circuitry (not shown) enclosed in housing 402 allow the sensing function of the optical sensor 410 to be controlled by IMD 400 and signal processing of signals responsive to detected light to be performed by IMD 400.

Lead 406 is shown coupled to connector block 404 allowing any electrodes or sensors carried by lead 406 to be electrically coupled to circuitry enclosed within housing 402. The lead 406 may correspond to lead 300 shown in FIG. 3 such that a lead-based optical sensor, including light emitting and/or detecting devices, can be coupled to IMD 400. It is recognized that in alternative embodiments, IMD 400 may be provided as a leadless device, without connector block 400, including only sensors/electrodes incorporated in housing 402. IMD 400 may be embodied as a monitoring-only device or may include therapy delivery capabilities, such as electrical stimulation or drug delivery capabilities, responsive to signals generated by sensor 410.

FIG. 5 is a functional block diagram of one example configuration of an IMD 516, such as similar to the IMD shown in FIG. 4. As shown, the IMD 516 may include a control module 581, a therapy delivery module 584 (e.g., a stimulation generator), a sensing module 586, and a power source 590. It will be recognized that this is merely an exemplary configuration and other configurations for IMDs are possible. For example, sensing apparatus and therapy delivery apparatus could be physically separate and autonomous devices that communicate with each other via telemetry.

The control module 581 may include a processor 580, memory 582, and a telemetry module 588. The memory 582 may include computer-readable instructions that, when executed, e.g., by the processor 580, cause the IMD 516 and the control module 581 to perform various functions attributed to the IMD 516 and the control module 581 described herein. Further, the memory 582 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 580 of the control module 581 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 580 herein may be embodied as software, firmware, hardware, or any combination thereof.

The control module 581 controls the therapy delivery module 584 to deliver therapy (e.g., electrical stimulation therapy to the heart) according to a selected therapy program, which may be stored in the memory 582. Specifically, the processor 580 of the control module 581 may control the therapy delivery module 584 to deliver electrical pulses with the amplitudes, pulse widths, frequency, and/or electrode polarities specified by the selected therapy program.

The therapy delivery module 584 may be coupled (e.g., electrically coupled) to therapy delivery apparatus 585. The therapy deliver apparatus 585 may include, among other therapy delivery devices, electrodes such as those shown on the lead of FIG. 3 and/or one or more housing electrodes such as those shown on the case 402 of IMD 400 in FIG. 4. The therapy delivery module 584 may be configured to generate and deliver electrical stimulation therapy, for example, to a heart. For example, the therapy deliver module 584 may deliver defibrillation shocks to the heart 12. Further, for example, the therapy delivery module 584 may deliver pacing pulses. In some examples, the therapy delivery module 584 delivers pacing, cardioversion, and/or defibrillation stimulation in the form of electrical pulses. Further, for example, therapy delivery module 584 may provide, for example, drug delivery therapy. For example, therapy delivery apparatus 585 may include therapy delivery elements (not explicitly shown) such as electrodes, catheters, drug delivery ports or the like for administering a therapy, etc. The present disclosure is not limited to any particular type of therapy, although one or more therapies may be more beneficial than others.

The sensing module 586 is coupled (e.g., electrically coupled) to sensing apparatus 587, e.g., to monitor signals from the sensing apparatus 587. The sensing apparatus 587 includes one or more optical sensors, such as those shown in FIGS. 1-4. Further, the sensing apparatus may include additional sensors used by IMD 516 for detecting patient conditions and making therapy delivery decisions, and/or for monitoring a patient's condition. In various embodiments, sensing module 587 may include an activity sensor, ECG sensing electrodes, pressure sensors, or other physiological sensors. The sensing apparatus 587 may include electrodes, such as those shown on the lead of FIG. 3 and/or one or more housing electrodes such as those shown on the case 402 of IMD 400 in FIG. 4, to monitor electrical activity of the heart, e.g., impedance signals between two or more electrodes, electrocardiogram (ECG) signals, etc.

Sensing module 586 may receive sensor signal(s) when enabled for sensing by control module 581. The sensing module 586 may perform, for example, pre-processing signal conditioning, such as analog filtering, and may provide optical sensor signals to processor 580 and/or may provide other sensor signals to processor 580 for use in monitoring physiological signals and detecting physiological events. The optical sensors of sensing apparatus 587 may be controlled via a control bus under the control of control module 581 (e.g., emission and detection using such optical sensors may be controlled, such as multiplexing of light emission by multiple light emitting devices, etc.).

The control of the light detecting devices and/or light emitting devices of optical sensors of sensing apparatus 587 will depend in part on the overall medical device architecture and hardware, firmware, and software employed. In one embodiment, processor 580 may receive the signals from an optical sensor and perform signal processing useful in just monitoring a patient condition and/or monitoring a patient condition and appropriately controlling therapy delivery module 584 in response thereto.

Various conductor elements extending from an optical sensor described herein may provide for connection to sensor driver circuitry and/or sensor processing circuitry (e.g., of sensor module 586) via any necessary connector elements, feedthroughs, etc. Sensor driver circuitry may provide the operational power for the optical sensor and control the timing of optical sensor operation. In one embodiment, sensor driver circuitry and sensor processor circuitry may operate as generally disclosed in U.S. Pat. No. 4,730,389 (Baudino et al.), hereby incorporated herein by reference in its entirety.

Further, for example, processor 580 may receive optical sensor signal output and process the signal output to determine one or more measurements of a physiological condition, such as blood oxygen saturation, glucose saturation, tissue perfusion or any other condition causing alterations in light modulation by the measurement body fluid or tissue volume. One or more embodiments of operation of such optical sensing and processing controlled by control module 581, for example, are generally provided in the U.S. Pat. No. 6,198,952 to Miesel entitled "Multiple Lens Oxygen Sensor for Medical Electrical Lead," which is incorporated by reference herein.

The one or more optical sensors of the sensing apparatus 587 may provide signals or values representative of one or more physiological parameters or conditions. Using such signals or values, and/or one or more other sensed activity, the IMD 516 (e.g., via the control module 581) may monitor a patient's condition, determine whether the patient is in need of therapy, determine whether therapy should be adjusted, etc. In some examples, the control module 581 may select the electrodes that function as sensing electrodes or optical sensors via a switch module within the sensing module 586, e.g., by providing signals via a data/address bus. In some examples, the sensing module 586 may include one or more sensing channels, each of which may include an amplifier. In response to the signals from the control module 581, the switch module of the sensing module 586 may couple the outputs from the selected electrodes or optical sensors to one or more of the sensing channels.

The telemetry module 588 of the control module 581 may include any suitable hardware, firmware, software, or any combination thereof for communicating with another device, such as a programmer (not shown). For example, under the control of the processor 580, the telemetry module 588 may receive downlink telemetry from and send uplink telemetry to the programmer with the aid of an antenna, which may be internal and/or external. The processor 580 may provide the data (e.g., data associated with the patient's condition or history of the patient) to be uplinked to the programmer and the control signals for the telemetry circuit within the telemetry module 588, e.g., via an address/data bus.

The various components of the IMD 516 are further coupled to a power source 590, which may include a rechargeable or non-rechargeable battery. A non-rechargeable battery may be selected to last for several years, while a rechargeable battery may be inductively charged from an external device, e.g., on a daily or weekly basis.

Figure 6:
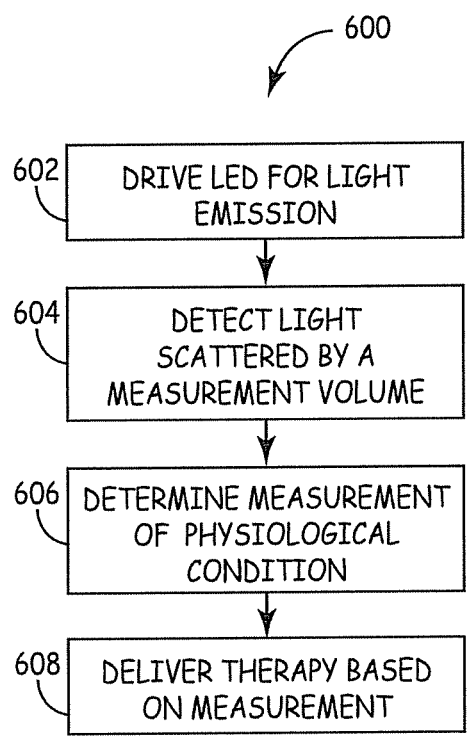
FIG. 6 is a block diagram of one exemplary embodiment of a method for delivering therapy using one or more measurements determined using an optical sensor, such as that shown in FIGS. 1 and 2.

A generalized method 600 for use in providing therapy is depicted in the flow diagram of FIG. 6. The exemplary method for delivering therapy 600 uses one or more measurements obtained with an optical sensor described herein. For example, at block 602 one or more optical sensor portions are driven to emit light. Thereafter, one or more light detecting devices detect light scattered by a measurement volume (e.g., a volume of fluid or tissue) (block 604). Measurements associated with a physiological condition are determined based at least on the detected light (block 606). Thereafter, therapy (e.g., stimulation therapy, drug therapy, etc.) may be delivered based on at least such optical measurements (block 608), or alternatively, such data may just be used for monitoring a patient's condition.

Method 600 is intended to illustrate the general functional operation of the devices and/or systems described herein, and should not be construed as reflective of a specific form of software or hardware necessary to practice methods described herein. It is believed that the particular form of software will be determined primarily by the particular system architecture employed in the device (e.g., IMD 516) and by the particular detection and therapy delivery methodologies employed by the device and/or system. Providing software and/or hardware to accomplish the described methods in the context of any modern IMD, given the disclosure herein, is within the abilities of one of skill in the art.

The techniques described in this disclosure, including those attributed to the IMD 516, the programmer, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An implantable medical device comprising:
    a hermetically sealed housing, wherein the hermetically sealed housing comprises one or more sensor openings defined therethrough;
    an optical sensor configured to generate a signal representative of a physiological condition, wherein the optical sensor comprises:
        a first optical sensor portion comprising at least one light emitting device and at least one light detecting device, wherein the at least one light emitting device and the at least one light detecting device are configured to emit light through a first optical window located within the one or more sensor openings and to detect light through the first optical window, respectively;
        a second optical sensor portion comprising at least one light emitting device and at least one light detecting device, wherein the at least one light emitting device and the at least one light detecting device are configured to emit light through a second optical window located within the one or more sensor openings and to detect light through the second optical window, respectively, wherein the at least one light emitting device of the first optical sensor portion is configured to emit light at a first wavelength and the at least one light detecting device of the second optical sensor portion is configured to detect light of the first wavelength, and further wherein the at least one light emitting device of the second optical sensor is configured to emit light of a second wavelength and the at least one light detecting device of the first optical sensor is configured to detect light of the second wavelength; and
    a control module coupled to the first and second optical sensor portions to control the emission and detection of light through the first and second optical windows.

2. The device of claim 1, wherein the first optical sensor portion comprises first and second light emitting devices, wherein each of the first and second light emitting devices of the first optical sensor portion are configured to emit light at a different wavelength of a first set of wavelengths, wherein the second optical sensor portion comprises first and second light emitting devices, wherein the first and second light emitting devices of the second optical sensor portion are configured to emit light at a different wavelength of a second set of wavelengths, wherein the first set of wavelengths is different than the second set of wavelengths, and further wherein the at least one light detecting device of the first optical sensor portion is configured to detect light of at least one of the second set of wavelengths through the first optical window and the at least one light detecting device of the second optical sensor portion is configured to detect light of at least one of the first set of wavelengths through the second optical window.

3. The device of claim 2, wherein the at least one light detecting device of each of the first and second optical sensor portions comprises a wideband light detector, and further wherein the control module is configured to control emission of light through the first and second optical windows in a time multiplexed manner.

4. The device of claim 2, wherein the at least one light detecting device of the first optical sensor portion comprises at least a first light detector tuned to one of the wavelengths of the second set of wavelengths and a second light detector tuned to another wavelength of the second set of wavelengths, and further wherein the at least one light detecting device of the second optical sensor portion comprises at least a first light detector tuned to one of the wavelengths of the first set of wavelengths and a second light detector tuned to another wavelength of the first set of wavelengths.

5. The device of claim 1, wherein the light emitting devices of the optical sensor are distributed between the first and second optical sensor portions such that the number of light emitting devices of the first optical sensor portion is equal to the number of light emitting devices of the second optical sensor portion or the number of light emitting devices of the first optical sensor portion is only one more than the number of light emitting devices of the second optical sensor portion.

6. The device of claim 1, wherein the housing is selected from the group consisting of:
   a. an elongated lead body, and
   b. an assembly that includes an implantable medical device case coupled to an elongated lead body.

7. The device of claim 1, wherein the first and second optical sensor portions are substantially of identical geometry with the optical path length between the at least one light emitting device of the first optical sensor portion and the at least one light detecting device of the second optical sensor portion being about equal to the optical path length between the at least one light emitting device of the second optical sensor portion and the at least one light detecting device of the first optical sensor portion.

8. An implantable medical device comprising:
   a hermetically sealed housing, wherein the hermetically sealed housing comprises one or more sensor openings defined therethrough;
   an optical sensor configured to generate a signal representative of a physiological condition, wherein the optical sensor comprises at least two optical sensor portions, each of the at least two optical sensor portions for emitting and detecting light through a corresponding optical window located within the one or more sensor openings, wherein each of the at least two optical sensor portions comprises at least one light emitting device to emit light through the corresponding window and at least one light detecting device to detect light through the corresponding window, wherein the number of light emitting devices in each optical sensor portion are equal or the number of light emitting devices of any one of the optical sensor portions is only one more than the number of light emitting devices of any other optical sensor portions, wherein the at least one light emitting device of each optical sensor portion emits light at a wavelength that is different than the at least one light emitting device of the other optical sensor portions and the at least one light detecting device of each optical sensor portion detects light at a wavelength emitted by at least one light emitting device of the other optical sensor portions; and
   a control module coupled to the optical sensor to control the emission and detection of light.

9. The device of claim 8, wherein each of the at least two optical sensor portions comprise two or more light emitting devices, each of the two or more light emitting devices configured to emit light at a wavelength different than the other light emitting devices of the optical sensor portion.

10. The device of claim 9, wherein the at least one light detecting device of each optical sensor portion comprises a wideband light detector, and further wherein the control module is configured to control emission of light in a time multiplexed manner.

11. The device of claim 9, wherein the at least one light detecting device of each optical sensor portion comprises at least a first light detector tuned to one of the wavelengths emitted by a different optical sensor portion and a second light detector tuned to another wavelength emitted by a different optical sensor portion.

12. The device of claim 8, wherein the housing is selected from the group consisting of:
   a. an elongated lead body, and
   b. an assembly including an implantable medical device case coupled to an elongated lead body.

13. The device of claim 8, wherein each of the at least two optical sensor portions are substantially of identical geometry with the optical path length between the at least one light emitting device of a first optical sensor portion and the at least one light detecting device of a second optical sensor portion being about equal to the optical path length between the at least one light emitting device of the second optical sensor portion and the at least one light detecting device of the first optical sensor portion.

14. The device of claim 8, wherein the at least one light detecting device of each optical sensor portion comprises a wideband light detector configured to detect light at a wavelength emitted by at least one light emitting device of the other optical sensor portions and to detect light emitted by the at least one light emitting device of the optical sensor portion with which it is co-located, and further wherein the control module is configured to monitor light output level of the at least one light emitting device of the optical sensor portion with which it is co-located and control variation of light output levels based on the monitored light output level.

15. A method for use in an implantable medical device having an optical sensor, wherein the optical sensor comprises at least two optical sensor portions, each of the at least two optical sensor portions for emitting and detecting light through a corresponding optical window, wherein each of the at least two optical sensor portions comprises at least one light emitting device to emit light through the corresponding window and at least one light detecting device to detect light through the corresponding window, wherein the number of light emitting devices in each optical sensor portion are equal or the number of light emitting devices of any one of the optical sensor portions is only one more than the number of light emitting devices of any other optical sensor portions, wherein the at least one light emitting device of each optical sensor portion emits light at a wavelength that is different than the at least one light emitting device of the other optical sensor portions and the at least one light detecting device of each optical sensor portion detects light at a wavelength emitted by at least one light emitting device of the other optical sensor portions, wherein the method comprises:
   enabling emission of light at a first wavelength by the at least one light emitting device of a first optical sensor portion of the at least two optical sensor portions for detection by at least one light detecting device of a different optical sensor portion; and
   enabling emission of light at a second wavelength by the at least one light emitting device of a second optical sensor portion of the at least two optical sensor portions for detection by at least one light detecting device of a different optical sensor portion.

16. The method of claim 15, wherein each of the at least two optical sensor portions comprise two or more light emitting devices, each of the two or more light emitting devices configured to emit light at a wavelength different than the other light emitting devices of the optical sensor portion.

17. The method of claim 15, wherein the corresponding window is disposed in one of an elongated lead body and a housing of an implantable medical device.

18. The method of claim 15, wherein each of the at least two optical sensor portions are substantially of identical geometry with the optical path length between the at least one light emitting device of a first optical sensor portion and the at least one light detecting device of a second optical sensor portion being about equal to the optical path length between the at least one light emitting device of the second optical sensor portion and the at least one light detecting device of the first optical sensor portion.

19. The method of claim 15, wherein the method further comprises providing a therapy to a patient based at least in part on light detected by the at least one light detecting device of the at least two optical sensor portions.

20. The method of claim 15, wherein the at least one light detecting device of each optical sensor portion comprises a wideband light detector configured to detect light at a wavelength emitted by at least one light emitting device of the other optical sensor portions and to detect light emitted by the at least one light emitting device of the optical sensor portion with which it is co-located, and further wherein the method comprises:

monitoring light output level of at least one light emitting device of an optical sensor portion using the at least one light emitting device co-located therewith; and controlling variation of light output levels of the at least one light emitting device co-located therewith based on the monitored light output level.

\* \* \* \* \*